US009855216B2

(12) United States Patent
Amoabediny et al.

(10) Patent No.: US 9,855,216 B2
(45) Date of Patent: Jan. 2, 2018

(54) TARGETED NANO-LIPOSOME CO-ENTRAPPING ANTI-CANCER DRUGS

(71) Applicants: Ghasem Amoabediny, Tehran OT (IR); Mohammad Mahdi Ochi, Tehran OT (IR); University of Tehran, Tehran OT (IR)

(72) Inventors: Ghasem Amoabediny, Tehran (IR); Mohammad Mahdi Ochi, Tehran (IR); Seyed Mahdi Rezayat, Tehran (IR); Azim Akbarzadeh, Tehran (IR); Bahman Ebrahimi, Tehran (IR)

(73) Assignees: Ghasem Amoabediny, Tehran (IR); Mohammad Mahdi Ochi, Tehran (IR); UNIVERSITY OF TEHRAN, Tehran (IR)

( * ) Notice: Subject to any disclaimer, the term of this patent is extended or adjusted under 35 U.S.C. 154(b) by 0 days.

(21) Appl. No.: 15/130,144

(22) Filed: Apr. 15, 2016

(65) Prior Publication Data
US 2016/0228362 A1    Aug. 11, 2016

Related U.S. Application Data

(60) Provisional application No. 62/166,694, filed on May 27, 2015.

(51) Int. Cl.
| | |
|---|---|
| A61K 9/127 | (2006.01) |
| A61K 31/19 | (2006.01) |
| A61K 31/357 | (2006.01) |
| A61K 31/704 | (2006.01) |
| A61K 45/06 | (2006.01) |
| A61K 31/353 | (2006.01) |

(Continued)

(52) U.S. Cl.
CPC ............ *A61K 9/127* (2013.01); *A61K 9/1271* (2013.01); *A61K 31/19* (2013.01); *A61K 31/353* (2013.01); *A61K 31/357* (2013.01); *A61K 31/704* (2013.01); *A61K 45/06* (2013.01); *A61K 47/6849* (2017.08); *A61K 47/6913* (2017.08); *C07K 16/2803* (2013.01); *A61K 9/1277* (2013.01); *A61K 9/5123* (2013.01);

(Continued)

(58) Field of Classification Search
None
See application file for complete search history.

(56) References Cited

U.S. PATENT DOCUMENTS 5,000,887 A  *  3/1991  Tenzel ................. A61K 9/1277
                                                        264/4.1
5,569,464 A     10/1996  Endo et al.
(Continued)

FOREIGN PATENT DOCUMENTS

| CN | 106692056 A * | 5/2017 | |
| WO | WO 0103668 A1 * | 1/2001 | ........... A61K 9/0073 |

OTHER PUBLICATIONS

K-J Kim, J-S Choi, K-W Kim, J-W Jeong. "The Anti-Angiogenic Activities of Glycyrrhizic Acid in Tumor Progression." Phytotherapy Research, vol. 27, 2013, pp. 841-846.*

(Continued)

*Primary Examiner* — Isaac Shomer
(74) *Attorney, Agent, or Firm* — NovoTechIP International PLLC

(57) ABSTRACT

A liposomal composition includes at least two anti-tumor herbal drugs that are simultaneously co-encapsulated. Optionally, the liposomal composition is targeted by adding a monoclonal antibody is added to the liposomes.

33 Claims, 25 Drawing Sheets

(51) Int. Cl.
*C07K 16/28* (2006.01)
*A61K 47/68* (2017.01)
*A61K 47/69* (2017.01)
*A61K 9/51* (2006.01)

(52) U.S. Cl.
CPC ........ *Y10S 977/773* (2013.01); *Y10S 977/906* (2013.01); *Y10S 977/907* (2013.01)

(56) References Cited

U.S. PATENT DOCUMENTS

| | | | |
|---|---|---|---|
| 2007/0116753 A1* | 5/2007 | Hong | A61K 9/0019 424/450 |
| 2007/0183983 A1* | 8/2007 | Morishita | A61K 9/0075 424/46 |
| 2010/0008937 A1* | 1/2010 | Peer | C12N 15/111 514/1.1 |
| 2010/0112040 A1* | 5/2010 | Basheer | A61K 9/127 424/450 |
| 2011/0177153 A1* | 7/2011 | Zhu | A61K 39/44 424/450 |
| 2011/0190623 A1* | 8/2011 | Li | A61K 9/1273 600/420 |
| 2012/0189678 A1 | 7/2012 | Li | |
| 2013/0157967 A1 | 6/2013 | Gundermann et al. | |

OTHER PUBLICATIONS

CWY Cheung, N Gibbons, DW Johnson, DL Nicol. "Silibinin—A Promising New Treatment for Cancer." Anti-Cancer Agnets in Medicinal Chemistry, vol. 10, 2010, pp. 186-195.*

CO Noble, Z Guo, ME Hayes, JD Marks, JW Park, CC Benz, DB Kirpotin, DC Drummond. "Characterization of highly stable liposomal and immunoliposomal formulations of vincristine and vinblastine." Cancer Chemotherapy and Pharmacology, vol. 64, 2009, pp. 741-751.*

D Dube, K Khatri, AK Goyal, N Mishra, SP Vyas. "Preparation and evaluation of galactosylated vesicular carrier for hepatic targeting of silibinin." Drug Development and Industrial Pharmacy, vol. 36(5), 2010, pp. 547-555. (Year: 2010).*

H Maheshwari, R Agrawal, C Patil, OP Katare. Abstract of "Preparation and pharmacological evaluation of silibinin liposomes." Arzneimittelforschung, vol. 53(6), 2003, pp. 420-427. (Year: 2003).*

Inventor Name Unknown. English Translation of CN106692056A. Translation obtained from https://patents.google.com/patent/CN106692056A/en on Sep. 19, 2017. 28 printed pages. Patent originally published in Chinese on May 24, 2017. (Year: 2017).*

Nitesh Kumar, Silymarin liposomes improves oral bioavailability of silybin besides targeting hepatocytes, and immune cells, Pharmacological Reports, Apr. 29, 2014, vol. 66, pp. 788-798.

Mohamed S. El-Samaligy, Evaluation of hybrid liposomes-encapsulated silymarin regarding physical stability and in vivo performance, International Journal of Pharmaceutics, Jun. 9, 2006, vol. 319, pp. 121-129.

Mohammed Eimowafy, Silymarin loaded liposomes for hepatic targeting: In vitro evaluation and HepG2 drug uptake, European Journal of Pharmaceutical Sciences, Jul. 12, 2013, vol. 50, pp. 161-171.

Xiaojuan Zhao, Optimization on condition of glycyrrhetinic acid liposome by RSM and the research of its immunological activity, International Journal of Biological Macromolecules, May 11, 2012, vol. 51, pp. 209-344.

* cited by examiner

TARGETED NANO-LIPOSOME CO-ENTRAPPING ANTI-CANCER DRUGS

CROSS REFERENCE TO RELATED APPLICATION

This application claims the benefit of priority from U.S. Provisional Patent Application Ser. No. 62/166,694, filed on May 27, 2015, and entitled "Smart Nano Phyto-Liposome Co-Entrapping Anti-Cancer Drugs And Bio-Conjugated with Monoclonal Antibody" which is incorporated by reference herein in its entirety.

SPONSORSHIP STATEMENT

This application has been sponsored by the Iranian Nanotechnology Initiative Council, which does not have any rights in this application.

TECHNICAL FIELD

The present application generally relates to the field of nano biotechnology and nano medicine, and more particularly to the production of targeted nano-liposome composition for treatment of cancers.

BACKGROUND

Various chemical anticancer drugs are known. Also known is that most have a range of unwanted side effects. Such side effects of the known chemical anticancer drugs are generally due to non-selective action, e.g., their toxicity to normal cells. Various herbal drugs and medicines, as treatments or potential treatments for cancer as well as a range of other conditions, are also known. Uses and potential uses of various ones of such herbal drugs and medicines have received additional attention in recent years as a potentially advantageous alternative for chemotherapy treatments. However, a significant problem with various herbal medicines is their slow action in treating an ailment.

For example, silymarin, a known standardized extract obtained from seeds of *Silybum marianum*, is used in treatment of liver diseases of varying origins. A primary antioxidant substance and main biological active compound of silymarin is silibinin. As another example, glycyrrhizic acid is the active principal aglycone of glycyrrhizin, which is the main active ingredient of *Glycyrrhiza Glabra* (licorice) roots. There is known interest in glycyrrhizic acid for potential anti-inflammatory activity, direct and indirect anti-viral activity, and anti-cancer activity. However, glycyrrhizic acid and silibinin have a low solubility in water, and therefore exhibit poor bioavailability.

Liposomes are a known drug delivery system. According to known techniques, liposomes can consist of lipid bilayers with an inside water phase, and can encapsulate both water soluble and lipophilic drugs. However, known liposome techniques have various shortcomings, including instability and insufficient loading efficacy Accordingly, in the field of liposomes, there is a need for increased efficiency and targeting of the drugs to the desired cells.

SUMMARY

The following brief summary is not intended to include all features and aspects of the present application, nor does it imply that the application must include all features and aspects discussed in this summary.

Disclosed compositions and methods include a liposome composition for use in the treatment of cancer, comprising at least one phospholipid compound; cholesterol; and at least two herbal drugs, wherein the at least two herbal drugs are co-encapsulated in the liposome composition. In an aspect, the at least one phospholipid compound can be composed of dipalmitoyl phosphatidyl choline (DPPC), and a poly (ethylene glycol)-phospholipid conjugate (PEG-lipid). In another aspect, the PEG-lipid can be distearoyl-phosphatidylethanolamine-N-[methoxy(polyethene glycol)-2000]. (DSPE-mPEG2000). In one aspect, the molar ratio of (DPPC):cholesterol:DSPE-mPEG2000 in the liposome can be in the range of about 7:3.5:0.3 to about 7:4:0.4.

In an aspect, the least two herbal drugs can include at least two mutually different members selected from the group consisting of silibinin, isosilibinin, silichristin, silidanin, glycyrrhizic acid, and glycyrrhetinic acid, and combinations thereof. In another aspect, one of the at least two herbal drugs can be silibinin and another of the at least two herbal drugs can be glycyrrhizic acid. In a related aspect, the molar ratio of the silibinin to glycyrrhizic acid can be in a range of about 1.5:1 to about 2:1. The liposome composition according to one or more disclosed aspects can have a negative zeta potential. In an aspect the liposome composition can have an average diameter of less than 50 nanometers.

Disclosed compositions and methods also include a liposome composition for use in the treatment of cancer, comprising at least one phospholipid compound; cholesterol; at least one monoclonal antibody; and at least two herbal drugs co-encapsulated in the liposome composition. In an aspect, the targeted liposome composition can have an average diameter of less than about 90 nanometers. In an aspect the at least two herbal drugs co-encapsulated in the liposome composition include at least two members selected from the group consisting of silibinin, isosilibinin, silichristin, silidanin, glycyrrhizic acid, and glycyrrhetinic acid and combinations thereof. In an aspect, of the at least two herbal drugs co-encapsulated in the liposome composition one can be silibinin, and another one of the at least two herbal drugs can be glycyrrhizic acid. The molar ratio of the silibinin to the glycyrrhizic acid, in an aspect, can be in the range of about 1.5:1 to about 2:1.

According to an aspect, the monoclonal antibody can be selected from the group consisting of anti-CD147 (HAb18), anti-CD166, anti-CD20, anti-HER2, anti-VEGF-A, anti-EGFR, and rituximab. The monoclonal antibody can, in an aspect be an Hab18 monoclonal antibody. In a related aspect, the effective number of Hab18 monoclonal antibody on the surface of the liposome can be at least 6. In another aspect, the phospholipid can be composed of DPPC, and a PEG-lipid). In a further aspect, the PEG-lipid can be DSPE-mPEG2000). The molar ratio of DPPC:cholesterol:DSPE-mPEG2000 in the liposome composition can be in the range of about 7:3.5:0.3 to about 7:4:0.4. The targeted liposome composition can have, in an aspect, a negative zeta potential.

Disclosed compositions and methods also include preparing a liposome composition, and the method can include step of mixing a lipid mixture with at least two herbal drugs, in a solvent; step of evaporating the solvent from a result of mixing the lipid mixture with at least two herbal drugs to form a lipid film; step of hydrating the lipid film with an aqueous solvent to form multilamellar vesicles; and step of sonicating the multilameral vesicles to form a co-encapsulated nano-liposome composition that simultaneously includes the at least two herbal drugs co-encapsulated. In an aspect, hydrating the lipid film with the aqueous solvent can be performed in a buffer. In another aspect, the mixture can include cholesterol and a phospholipid compound. In an aspect, the step or portions of the step of hydrating the lipid film with the aqueous solvent can be performed in a buffer, and wherein the specific weight ratio of the at least two herbal drugs:the lipid mixture: the aqueous solvent in the buffer being in the range of about 1:2:7 to about 1:3:11. In an aspect, the method can also include drying of the liposome composition.

According to aspects the method can also include targeting the liposome composition. Targeting the liposome composition can include forming of micelles; coupling a monoclonal antibody to the micelles; and transferring of the monoclonal antibody coupled to the micelles to the prepared liposome composition to form a targeted liposome composition.

BRIEF DESCRIPTION OF THE DRAWINGS

This application will be understood more clearly from the following description and the accompanying figures. These figures are given purely by way of an indication and in no way restrict the scope of the application. Of these figures.

DETAILED DESCRIPTION

The following detailed description enables persons of ordinary skill in the art pertaining to the Technical Field skilled in the art to make and use the teachings of the instant application. For purposes of explanation, specific examples are set forth to assist persons of ordinary skill in the relevant art disclosed concepts, an present application. However, it will be apparent to one skilled in the art that these specific details are not required to practice the teachings of the instant application. Descriptions of specific applications are provided only as representative examples. Various modifications to the described implementations will be readily apparent to one skilled in the art, and the general principles defined herein may be applied to other implementations and applications without departing from the scope of the present application. The present application is not intended to be limited to the implementations shown, but is to be accorded the widest possible scope consistent with the principles and features disclosed herein.

In one general aspect, a liposomal composition is formed, having liposomes in which at least two herbal drugs are co-encapsulated simultaneously. For purposes of description, liposomes according this disclosure, in which at least two herbal drugs are co-encapsulated simultaneously, will be referred to as "co-encapsulated nano-liposomes." It will be understood that the term "co-encapsulated nano-liposomes" is only a label for convenience; it adds no descriptive content to this disclosure and places no limitation on the appended claims. In an aspect, co-encapsulated nano-liposomes according to this disclosure can be prepared as a PEGylated nano-liposome composition in which at least two herbal drugs are co-encapsulated simultaneously. In another aspect, co-encapsulated nano-liposomes can be targeted, by adding an antibody to their surface. The antibody can be, for example, a monoclonal antibody. One example according this aspect can be a targeted PEGylated co-encapsulated nano-liposome. Benefits provided by targeted co-encapsulated nano-liposomes, for example the targeted PEGylated co-encapsulated nano-liposome composition, is increased delivery effectiveness to the target cells.

EXAMPLE

Figure 1:
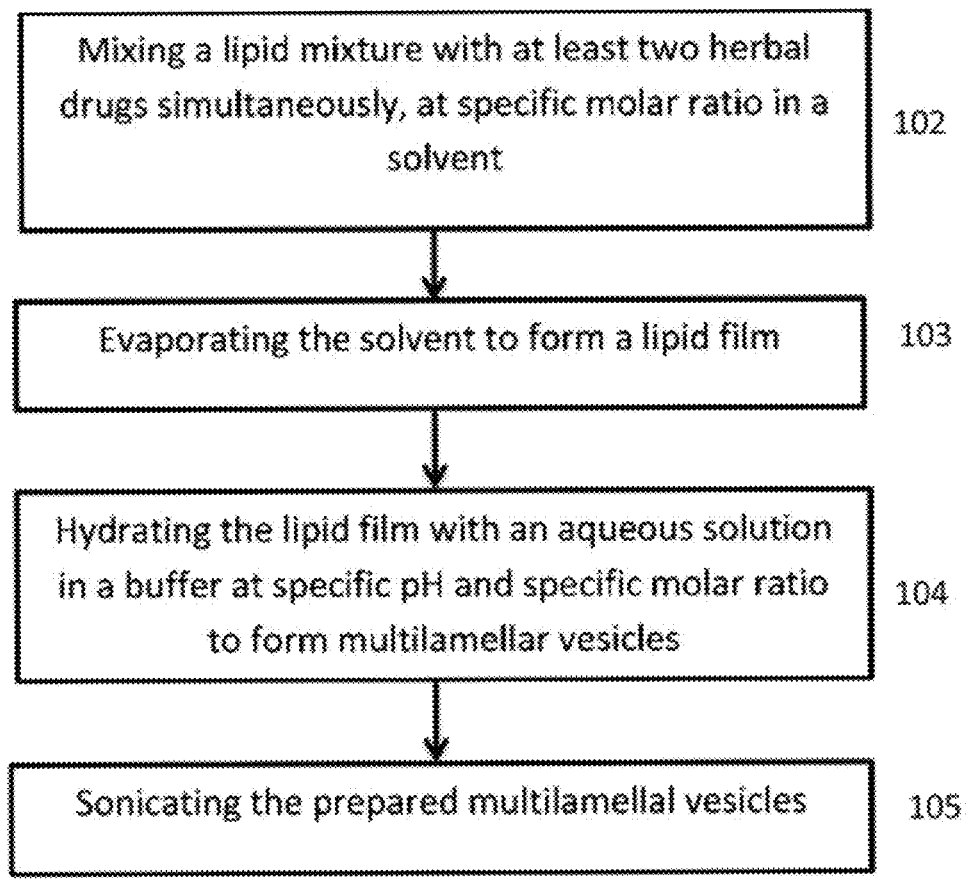
FIG. 1 is one example flow diagram representing a process for preparing a co-encapsulated nano-liposome according to one or more aspects.

FIG. 1 shows one example flow chart representing one process for producing a co-encapsulated nano-liposome according to one or more aspects.

Referring to FIG. 1, at step 102 a lipid mixture is mixed with at least two herbal drugs simultaneously. In some implementation of the present application, the lipid mixture is composed of cholesterol and a phospholipid compound where the phospholipid compound preferably is dipalmitoyl phosphatidyl choline (DPPC), and a poly (ethylene glycol)-phospholipid conjugate (PEG-lipid).

Various herbal drugs with anti-tumor properties can be used in this composition including: silibinin, isosilibinin, silichristin, silidanin, glycyrrhizic acid and glycyrrhetinic, and combinations thereof. In one implementation, silibinin and glycyrrhizic acid are used.

The molar ratio of the herbal drugs to the lipid mixture is an important factor, as it has effects on final product efficiencies. In one example, a molar ratio of DPPC:cholesterol: DSPE-mPEG2000 in the liposome composition is in the range of about 7:3.5:0.3 to about 7:4:0.4. In one example, using various specific herbal drugs, the molar ratio of those drugs, silibinin, and glycyrrhizic acid was in in the range of 1.5:1 to about 2:1.

In an implementation, an organic solvent such as ethanol can be used to dissolve the lipid mixture and the herbal drugs.

Referring to FIG. 1, at step 103 a lipid film is formed by evaporating the solution, for example, using a rotary evaporator.

Next, at step 104, the lipid film formed according to step 103 is hydrated. The hyrading for example by using an aqueous solvent in a buffer. In one implementation of step 104, maltose can be used as an aqueous solvent and HEPES used as a buffer. Regarding the PH in which the hydration is implemented, one example can be in the range of 5 to 7 and, preferably, can be in the range of 5 to 6. Regarding weight ratio of the herbal drugs:lipid phase, one example is in the range of about 1:2:7 to 1:3:11.

Referring to FIG. 1, at step 104 sonication can decrease the mean diameter of the formed multilamellar vesicles. In some implementations, filtration can be used for synthesis of small unilamellar vesicles or nano-liposomes. The prepared co-encapsulated nano-liposome composition according to step 105 is can be in suspension form. In an aspect, the nano-liposome composition can be dried. For example, in one implementation, partial suspension was freeze-dried at about −48° C. for around 48 hours.

The suspension form of co-encapsulated nano-liposomes of the present application shows a suitable stability. For example, in a buffer solution at 4° C., the mean diameter of said co-encapsulated nano-liposomes remained in the range of about 50 to about 60 nm after 3 months.

Figure 2:
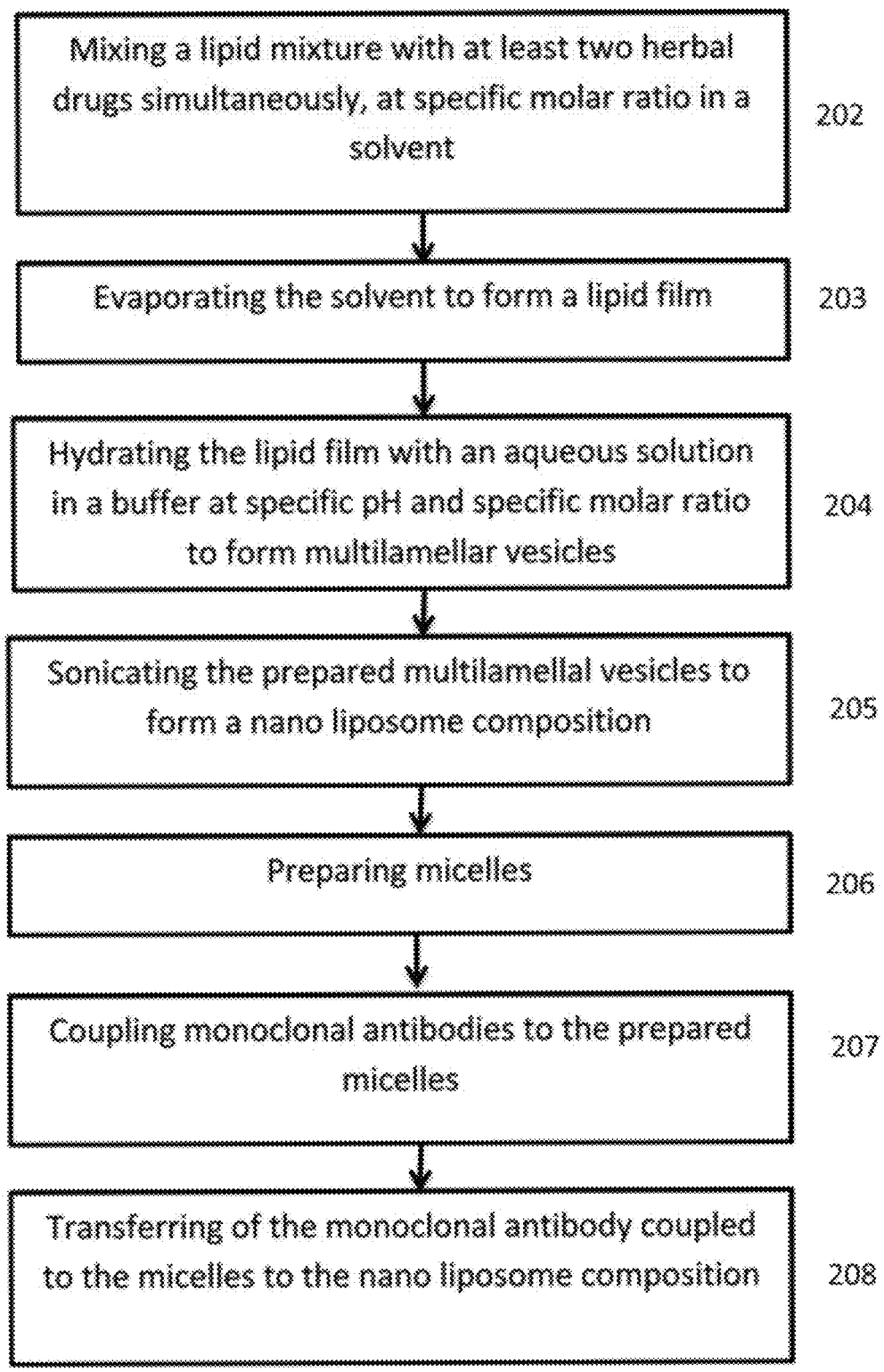
FIG. 2 is one flow diagram representing a process for preparing a targeted co-encapsulated nano-liposome according to one or more aspects.

FIG. 2 is a flow diagram of one process for preparing targeted co-encapsulated nano-liposomes. A process according to the FIG. 2 flow diagram can be an extension of the process described in reference to FIG. 1, with added steps for incorporating an antibody into the co-encapsulated nano-liposome. For example, referring to FIG. 2, step 202 through step 205 can be performed similarly to, or identically to step 102 through 105 of FIG. 1. Accordingly, in one implementation, after step 205 a process according to FIG. 2 can provide a co-encapsulated nano-liposome composition as described in reference to FIG. 1. Steps 206 to 208 are further steps for targeting the prepared co-encapsulated nano-liposome resulting from step 205, and will now be described.

Referring to FIG. 2, at step 206 a lipid mixture is prepared. In one implementation, the NHS-PEG-DSPE and mPEG2000-DSPE are used as lipid mixture. The prepared lipid mixture is dissolved in a buffer in special concentration, and then the dissolved mixture is heated. In some implementation, HEPES can be used as a buffer.

With reference to step 207, a monoclonal antibody can be mixed with the lipid mixture. The monoclonal antibody is selected based on the target organ (e.g., liver, brain, pancreas). The selection can be, for example, from among anti-CD147 (HAb18), anti-CD166, anti-CD20, anti-HER2 (such as trastuzumab), anti-VEGF-A (such as bevacizumab, ranibizumab), anti-EGFR (such as cetuximab), rituximab, etc. For example, if the liver is the target organ, HAb18 can be the selected monoclonal antibody, as Hab18 showed high affinity to liver cancer, based on a long-term research of immune-targeting medicine for liver cancer. Regarding the molar ratio of monoclonal antibody to the lipid mixture, one example is in the range of 1:5 to 1:15 and preferably 1:10

A process according to the FIG. 2 flow diagram can then proceed to step 208, at which the prepared monoclonal mixture of step 207 is mixed with the co-encapsulated nano-liposome prepared according to steps 202 to 205, to transfer monoclonal antibodies to the surface of nano-liposomes. In an aspect, in step 208 the mixture containing monoclonal antibody can be incubated with the pre-formed co-encapsulated nano-liposome, which produces targeted co-encapsulated nano-liposomes Regarding diameters of targeted co-encapsulated nano-liposomes, one example range can be from about 60 nm to about 90 nm. Regarding diameter of the monoclonal antibody, one example range for the HAb18 described above can be about 14 nm to about 16 nm.

One example application of the co-encapsulated nano-liposome and targeted co-encapsulated nano-liposome described hereinabove can be treatment of hepatocellular carcinoma (liver cancer). Another example application of the co-encapsulated nano-liposome and targeted co-encapsulated nano-liposome described hereinabove can be treatment of other liver damage conditions, for example, viral hepatitis.

Example 1

Preparation of Co-Encapsulated Nano-Liposomes

Non-targeted co-encapsulated nano-liposomes were prepared by a first thin layer film process, hydration method using a HEPES buffer, and finally sonication. For the preparation of liposomes co-encapsulating two herbal drugs in the present example, a mixture of DPPC:cholesterol: DSPE-mPEG2000 with about 7:4:0.36 molar ratio was prepared. Then, the herbal drugs containing silibinin and glycyrrhizic acid at molar ratio of about about 1.5:1 to about 2:1 as the lipophilic phase were dissolved in ethanol. The fluorescent label (DIL) was incorporated in the lipid bilayer with 0.1 mol % for fluorescent microscopy analysis. The organic solvent was evaporated using a rotary evaporator to produce a thin lipid film. Before hydration, the lipid film was flushed with nitrogen. Liposomes were formed by hydration of the lipid film with maltose solution in HEPES buffer (10 mill molar (mM), pH 5.5) as hydrophilic phase and were heated to about 51° C. The weight ratio of herbal drugs:lipid phase:maltose is about 1:2.5:9 (w/w) weight ratio. The mean diameter of the liposome decreases with sonication. Multi-lamellar vesicles sonicated at 60% amplitude for 10 (minutes (10 seconds on, and 15 seconds off) and filtration for synthesis of small unilamellar vesicles (SUV) or nano-liposomes. The partial of suspension was then freeze-dried at about −48° C. for around 48 hours.

Example 2

Targeting Co-Encapsulated Nano-Liposomes
Forming of Micelles

In one example of forming micelles, lipid mixtures, composed of NHS-PEG2000-DSPE and mPEG2000-DSPE at about 1:4 molar ratio, were dissolved in a HEPES buffer (10 mM, pH 5.5) with a concentration above the Critical Micelle Concentration (CMC) of the lipids and were heated for 10 min in a water bath with a temperature of around 60° C. with occasional gentle vortexing.

Monoclonal Antibody HAb18 Coupling to Micelles

The monoclonal antibody HAb18 and NHS-PEG2000-DSPE (Monoclonal Antibody HAb18: NHS-PEG2000-DSPE in about 1:10 moles ratio) were dissolved in a HEPES buffer (10 mM, pH 5.5) and stirred for about 24 hours at room temperature.

Transfer of Monoclonal Antibody HAb18 from Micelles to Nano-Liposomes

Micelles were then incubated with pre-formed liposomes containing 3 mol % PEG for 1 hours at 60° C. Transfer from HAb18 micelle conjugates into nano-liposomes was examined for nano-liposomes containing 3.51 mol % of mPEG. The antibody incorporation was about 16.30 microgram antibody/micro mol liposome.

Figure 3A:
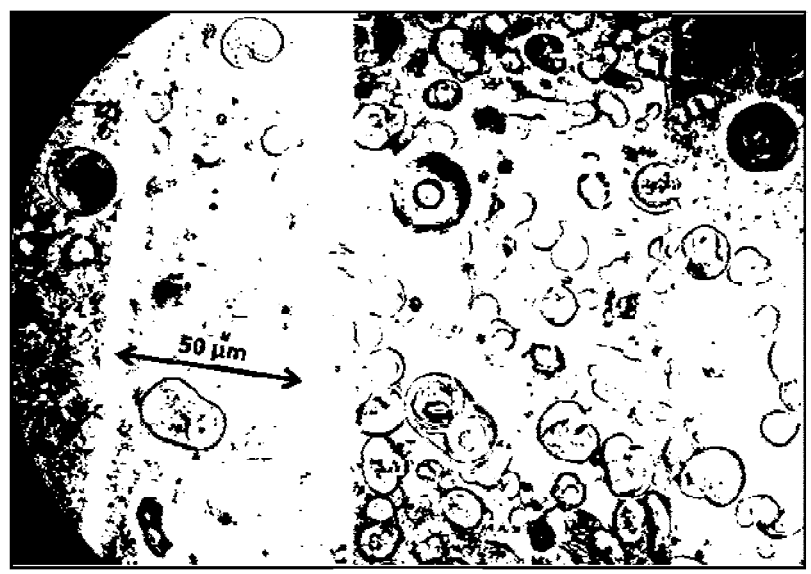
FIG. 3A Illustrates a fluorescent microscopic image of co-encapsulated multilamellar vesicles in a process according to one or more aspects.
Figure 3B:
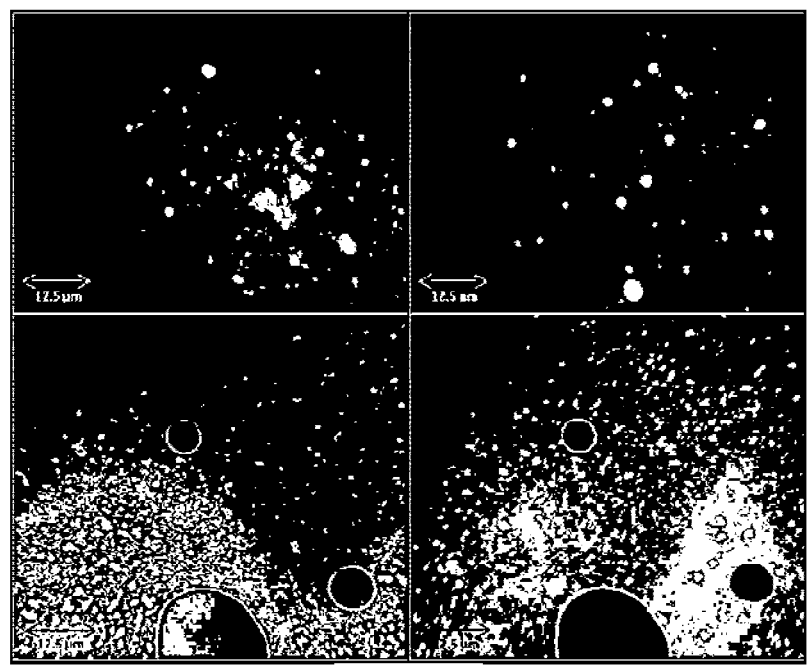
FIG. 3B Illustrates a fluorescent microscopic image of co-encapsulated multilamellar vesicles before decreasing size of liposomes, in a process according to one or more aspects.

FIGS. 3A and 3B illustrate the in vitro morphology and multi membranes of liposomal herbal drugs in micrometric size before sonication and synthesis of small uni-lamellar vesicles. FIG. 3A illustrates the light microscopic image of silibinin and glycyrrhizic acid multilamellar vesicles, where FIG. 3B shows fluorescenct microscopic image of silibinin and glycyrrhizic acid multilamellar vesicles. As illustrated in these figures, the sizes of liposomes are presented in micrometers.

The particle size and zeta potential of non-targeted and targeted co-encapsulated nano-liposomes were also determined by dynamic light scattering (DLS) and a zeta analyzer. The effect of herbal drugs entrapment and targeting on the size, and the zeta potential of nano-liposomes is indicated by the data presented and set forth in TABLE 1, herein below. Data are presented as mean±standard error.

TABLE 1

| Liposomal suspension | Mean Particle size nm (Std. Error) | Mean zeta potential mV (Std. Error) |
| --- | --- | --- |
| Nano-liposome without herbal drugs | 44 (±2.2) | −31.66 (±0.39) |
| Co-encapsulated nano-liposomes after 3 days | 46.3 (±0.4) | −23.25 (±0.83) |
| Co-encapsulated nano-liposomes after 3 months | 58.2 (±3.8) | −25.52 (±0.97) |
| Targeted co-encapsulated nano-liposomes with HAb18 | 86.5 (±5) | −0.74 (±0.1) |

The formulation of PEGylated nano-liposomes sonicated at 60% amplitude showed a narrow size distribution with an average diameter of 46.3 nm. The zeta potential of the co-encapsulated nano-liposome was about −23.25 mV. It was observed that zeta potential of co encapsulated nano-liposome have sufficient charge to inhibit aggregation of liposomes The co-encapsulated nano-liposomes of the present application show a suitable stability, for example in a buffer solution at 4° C., the mean diameter of said co-encapsulated nano-liposomes is about 58.2 nm after 3 month.

It can be understood from data summarized in TABLE 1 formation of targeted co-encapsulated PEGylated nano-liposome composition in which two anti-tumor herbal drugs are co-encapsulated simultaneously and bio-conjugated to monoclonal antibody HAb18/Anti-CD147, has a mean diameter of about 86.5 nanometers well as negative zeta potential. Therefore, according to data summarized in TABLE 1, loading of silibinin and glycyrrhizic acid, leads to increase of the mean diameter and decreasing zeta potential negative charge of nano-liposome. Mean diameter and zeta potential data summarized in aforementioned TABLE 1 are obtained from about 150 individual liposomes.

The micelles composed of mPEG2000-DSPE and NHS-PEG2000-DSPE (which are in ratio of about: 4:1, mol/mol in the micelles) had a diameter of 11-12 nm. Following coupling with HAb18, the micelle diameter increased to approximately 33-59 nm.

Entrapment efficiency of nano-liposomes co-encapsulating herbal drugs of silibinin and glycyrrhizic acid was detected using a High-performance liquid chromatography (HPLC) method. A reversed phase of C18 column was used. The mobile phase consisted of a mixture of acetonitrile and phosphoric acid (0.1%) (51:49, v/v) delivered at a flow rate of 1.00 ml/minute. First, to remove all free drugs, the co-encapsulated nano-liposomes were dialyzed with dialysis membrane (12,000-14,000 Da, molecular weight cut off) against the buffer. Then, 200 μl of methanol was added to 100 μl aliquots of the extruded suspension in tubes, and was mixed followed by sonication for 10 minutes. Then, 60 μl of the supernatant was analyzed by the HPLC system. The absorbance of the silibinin and glycyrrhizic acid were measured in an ultraviolet-visible spectrometer that is used for HPLC method, in the range of 200-350 nm. Column elute was monitored spectrophotometrically at the wavelength of 240 nm with a UV detector. The calibration curves of silibinin and glycyrrhizic acid were linear over the range of standard concentrations of 0.125, 0.25, 0.5 mgr/ml with a correlation coefficient of $R2>0.97$ and $R2>0.99$, respectively. The encapsulation efficiency measures liposomes ability to encapsulate drugs, based on the amount of placed drug during the production and the amount of drug in the liposome.

Figure 4A:
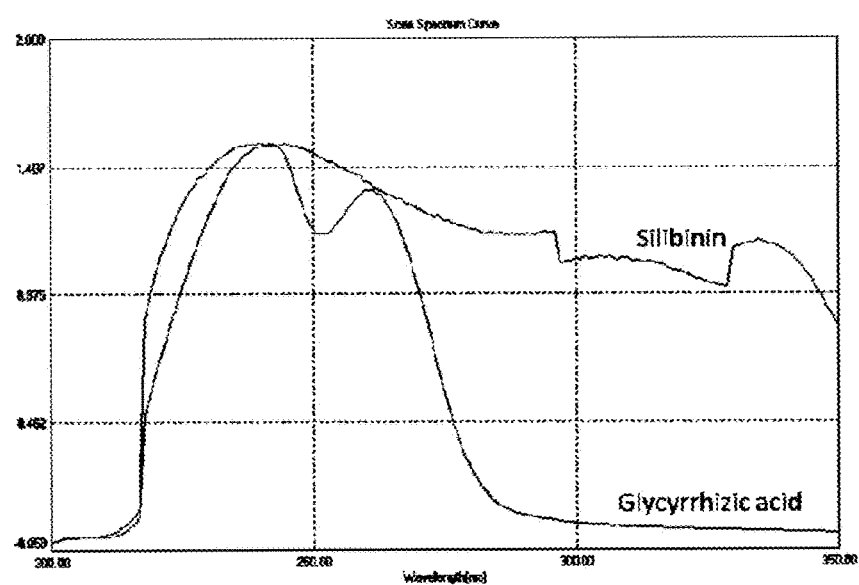
FIG. 4A illustrates absorbance peak of silibinin and glycyrrhizic acid, confirming loading of herbal drugs in a co-encapsulated nano-liposome composition according to one or more aspects.
Figure 4B:
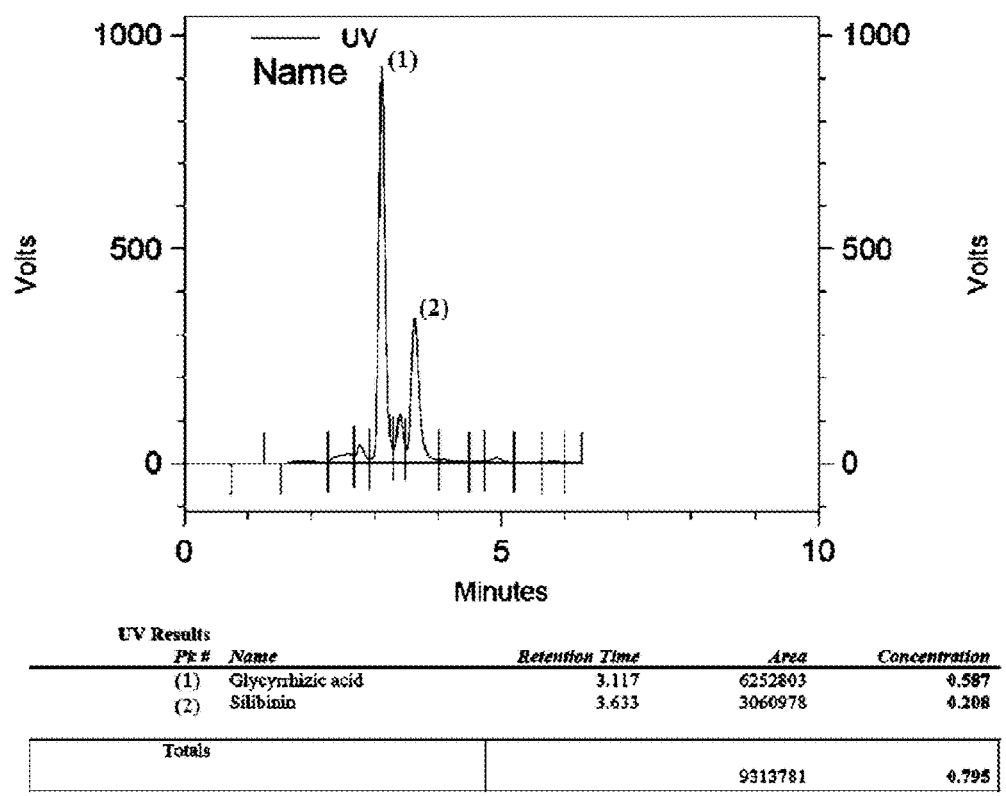
FIG. 4B illustrates the high-performance liquid chromatography (HPLC) graph of the silibinin and glycyrrhizic acid concentration peaks and shows loading of herbal drugs in the co-encapsulated nano-liposomes according to one or more aspects.

FIG. 4A illustrates the absorbance peak of silibinin and glycyrrhizic acid at the wavelength of 240 nm and confirms the used anti-tumor herbal drugs were loaded in the liposomal composition. FIG. 4B illustrates the HPLC graph of glycyrrhizic acid and silibinin concentration peaks in which glycyrrhizic acid denoted by (1) and silibinin denoted by (2). This Figure shows the loading order of herbal drugs in the nano-liposomes. The encapsulation efficiency determined by this method was about 25% for silibinin and was about 68.78% for glycyrrhizic acid.

Drugs release rate from the prepared nano-liposome composition was measured by HPLC method. The ability of release silibinin and glycyrrhizic acid at pH 5.5 and at pH 7.4 was also evaluated. For this aim, 1 mL of liposomal suspension was placed into a dialysis bag of cellulose with 12,000-14,000 Da, molecular weight cut off (using the membranes of Filtration Products, Inc.). The dialysis bags were placed in 50 mL of HEPES buffer (pH 5.5) and phosphate buffered saline (pH 7.4) separately, the media stirred with a magnetic bar at 100 rpm at 37° C., 200 μL of the suspension were removed at different times and measured by HPLC method, in the range of 240 nm.

Figure 5A:
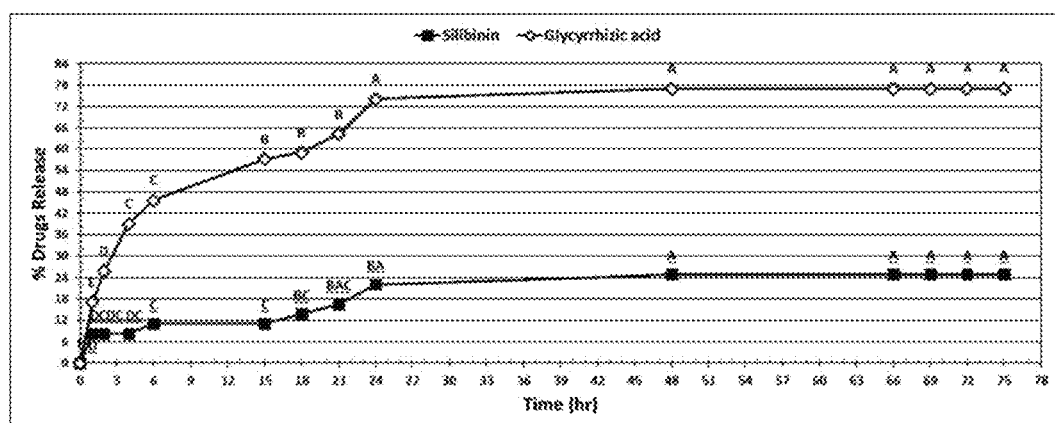
FIG. 5A illustrates the in vitro silibinin and glycyrrhizic acid release, of co-encapsulated nano-liposomes according to one or more aspects, at pH 5.5.
Figure 5B:
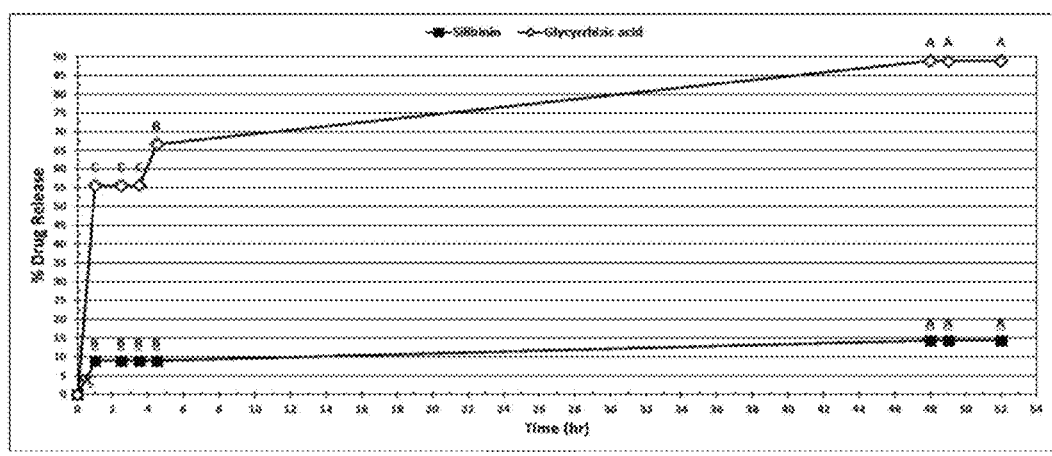
FIG. 5B illustrates the in vitro silibinin and glycyrrhizic acid release, of co-encapsulated nano-liposomes according to one or more aspects at pH, 7.4.

In vitro controlled release rate of silibinin and glycyrrhizic acid from co-encapsulated PEGylated nano-liposome is sensitive in the pH range of about 5 to about 7. FIG. 5A shows the in vitro silibinin and glycyrrhizic acid release at a pH of 5.5. FIG. 5B shows the same release at a pH of 7.4.). In these figures, data with different letters demonstrate significantly variable (P<0.05) from each other. As represented in these figures, more release percent was obtained at PH of 5.5 immediately after applying (about two hours after using The pH sensitive of in vitro controlled release rate of silibinin and glycyrrhizic acid at pH 5.5 (% 5) from co-encapsulated PEGylated nano-liposome ccomposition is represented in more details in TABLE. 2.

TABLE 2

In vitro release of silibinin and glycyrrhizic acid at pH 5.5 (%5)*

| Time (hour) | % Glycyrrhizic acid release | % Silibinin release |
|---|---|---|
| Control | 0 F | 0 D |
| 1 | 17.12 E | 8.29 DC |
| 2 | 25.67 D | 8.29 DC |
| 4 | 39 C | 8.29 DC |
| 6 | 45.66 C | 11.05 C |
| 15 | 57.07 B | 11.05 C |
| 18 | 58.97 B | 13.81 BC |
| 21 | 64.21 B | 16.58 BAC |
| 24 | 74.19 A | 22.10 BA |
| 48 | 77.05 A | 24.87 A |
| 66 | 77.05 A | 24.87 A |
| 69 | 77.05 A | 24.87 A |
| 72 | 77.05 A | 24.87 A |
| 75 | 77.05 A | 24.87 A |

*A p-value of <0.05 was considered significant

The morphology (shape, structure and size) of the nano-liposomes was analyzed by scanning electron microscopy (SEM) and transmission electronic microscopy (TEM) and observed results are illustrated in FIG. 6A through FIG. 8. The formation and structure of liposomes were verified through their morphological aspect, which was examined using TEM.

Figure 6A:
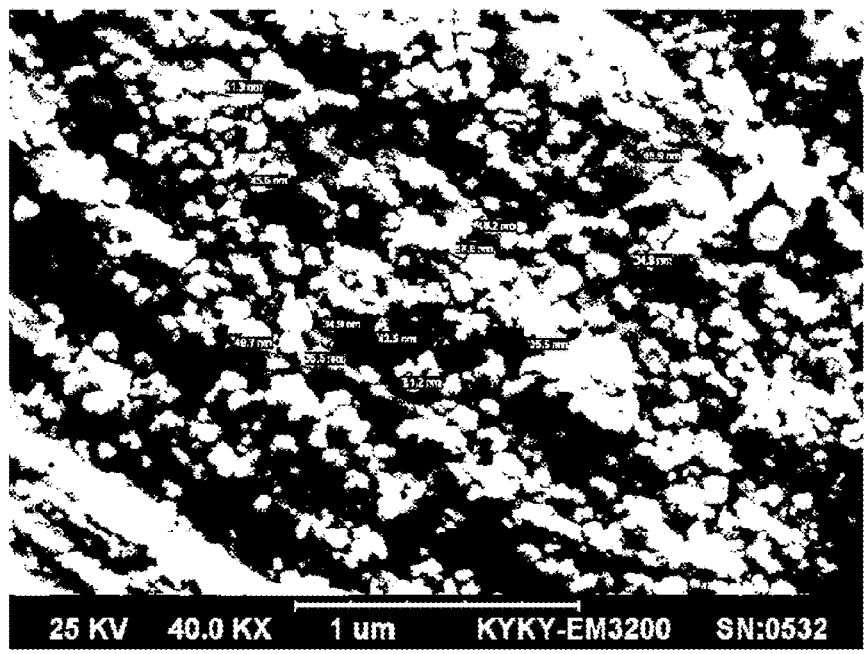
FIG. 6A is the scanning electron microscope (SEM) image of co-encapsulated nano-liposomes according to one or more aspects.
Figure 6B:
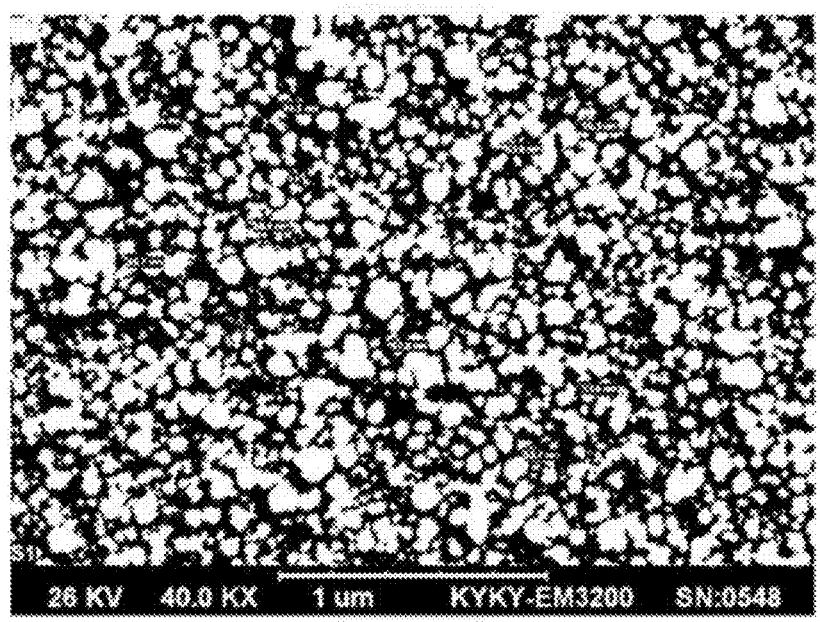
FIG. 6B is SEM image of co-encapsulated nano-liposomes according to one or more aspects, after 3 months.

FIG. 6A illustrates the SEM image of co-encapsulated nano-liposomes. As is indicated by this figure, the mean diameter of co-encapsulated nano-liposomes was 43 nm. FIG. 6B illustrates the SEM image of the co-encapsulated nano-liposomes after 3 months. As is indicated by this figure, the mean diameter of co-encapsulated nano-liposomes is 55.36 nm.

Figure 7A:
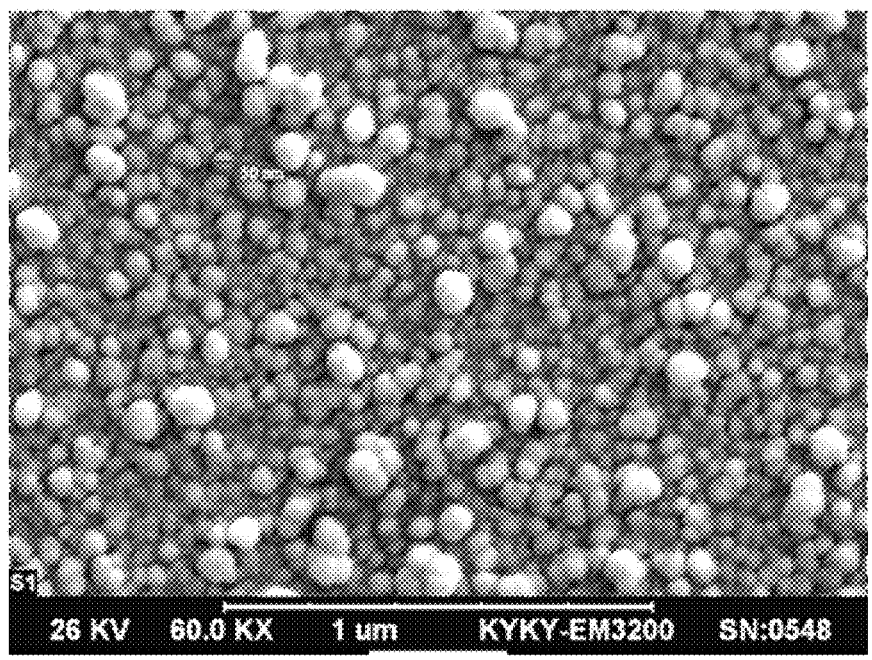
FIG. 7A is the SEM image of non-targeted co-encapsulated nano-liposomes according to one or more aspects.
Figure 7B:
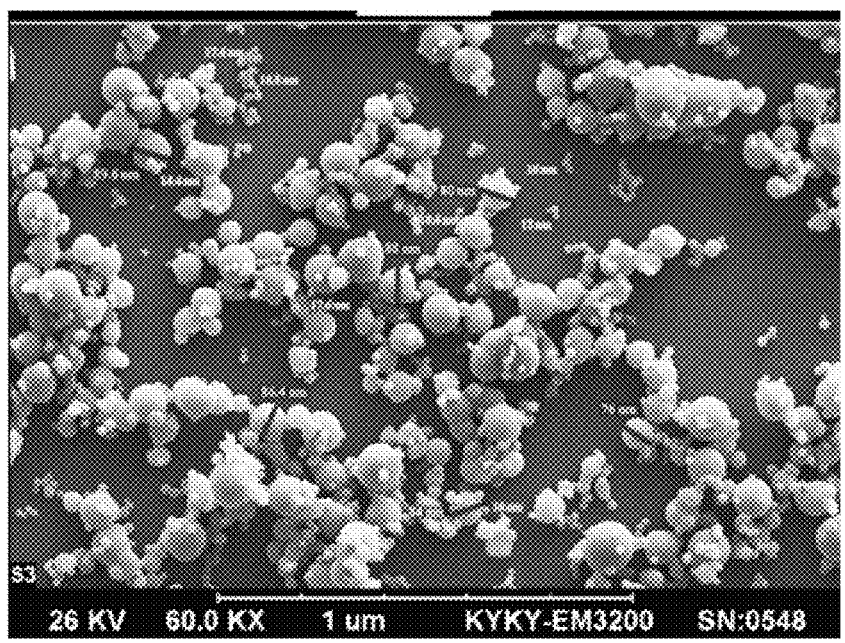
FIG. 7B is the SEM image of targeted co-encapsulated nano-liposomes with the monoclonal antibody (HAb18) according to one or more aspects.

With reference now to FIG. 7A, this figure illustrates the SEM images of exemplar non-targeted co-encapsulated nano-liposomes. FIG. 7B illustrates the SEM images of exemplar targeted co-encapsulated nano-liposomes with HAb18. As can be seen by proportional differences in features between FIGS. 7A and 7B, mean diameter of targeted co-encapsulated nano-liposomes with HAb18 is about 84 nm and the mean diameter of monoclonal antibodies HAb18 is about 16.1 nm. This reflects suitable bioconjugation of about 6 HAb18 monoclonal antibodies to co-encapsulated nano-liposome with mean diameter of about 80 nm.

Figure 8A:
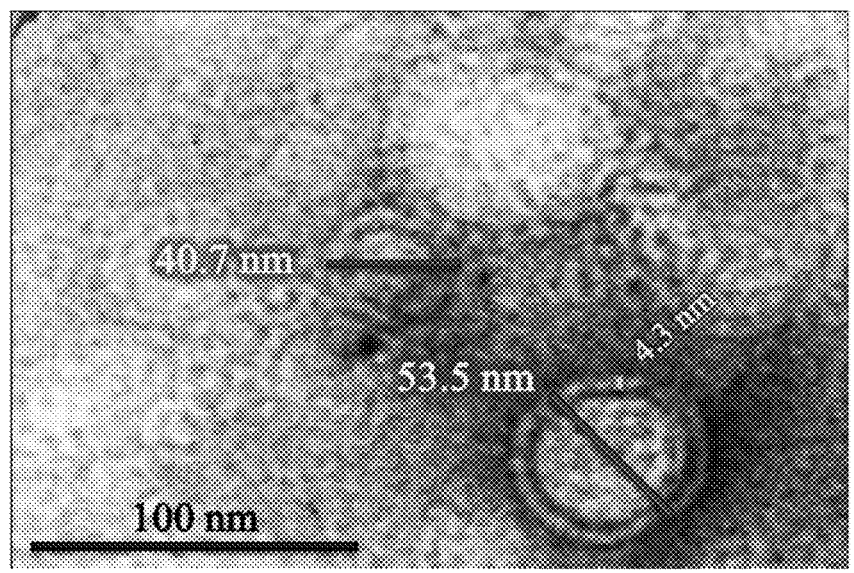
FIG. 8A illustrates the transmitting electron microscope (TEM) image of non-targeted co-encapsulated nano-liposomes according to one or more aspects.
Figure 8B:
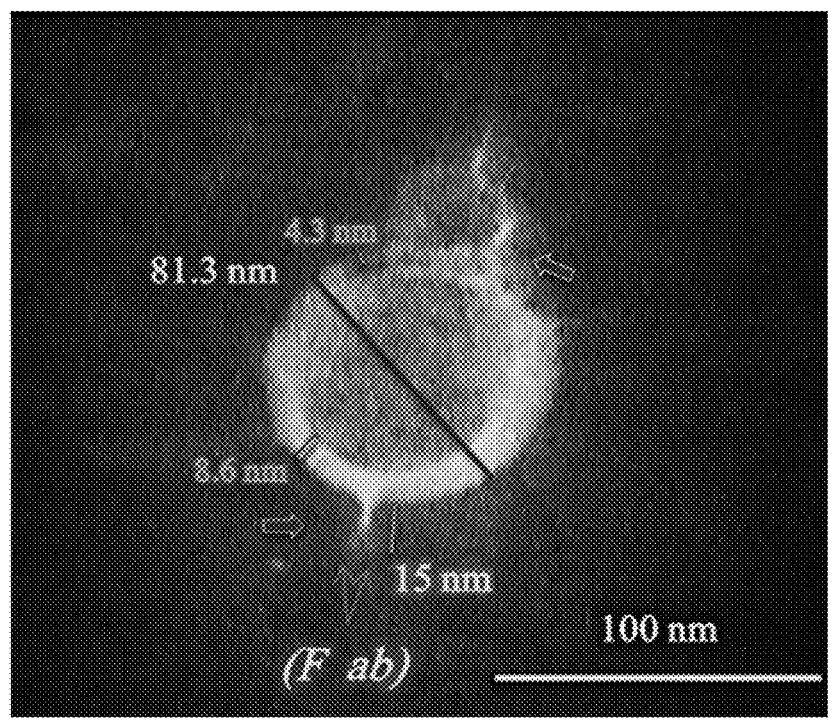
FIG. 8B is the TEM image of targeted co-encapsulated nano-liposomes with the monoclonal antibody (HAb18), according to one or more aspects.

FIG. 8A illustrates the TEM images of non-targeted co-encapsulated nano-liposomes. FIG. 8B, in contrast, illustrates TEM images of targeted co-encapsulated nano-liposomes with HAb18 are illustrated. As seen from comparing FIGS. 8A and 8B, the range of diameter of co-encapsulated nano-liposomes is less than about 60 nm, and the diameter of targeted co-encapsulated nano-liposomes is less than about 81 nm and the diameter of monoclonal antibody HAb18 is about 15 nm with a Y shape. Diameter measurement of the Fab or Fc domain of HAb18 monoclonal antibody by TEM photograph is around 8 nm.

The co-encapsulated nano-liposomes were analyzed by ATR-FTIR. FTIR results demonstrated PEGylating surface of co-encapsulated nano-liposomes.

Figure 9A:
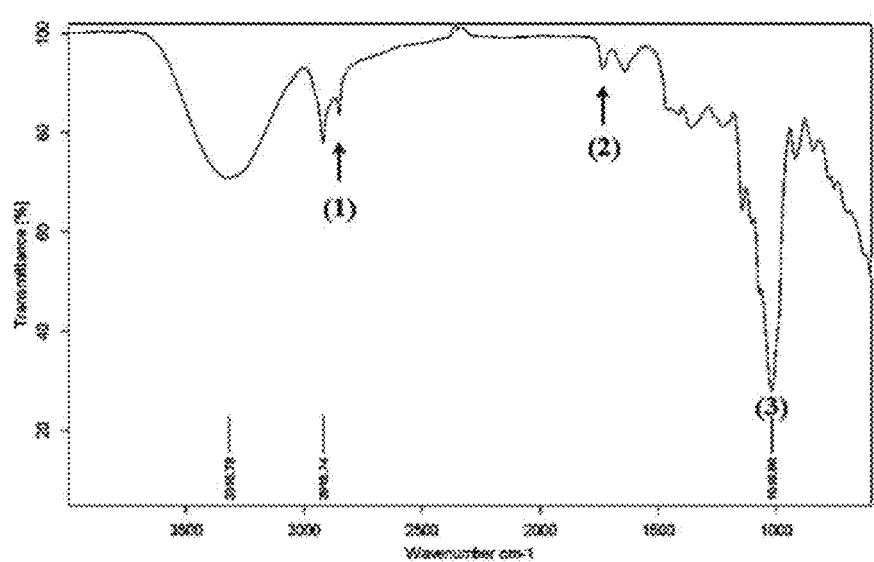
FIG. 9A illustrates the attenuated total reflectance Fourier transform infrared spectroscopy (ATR-FTIR) of PEGylated surface of the nano-liposome.
Figure 9B:
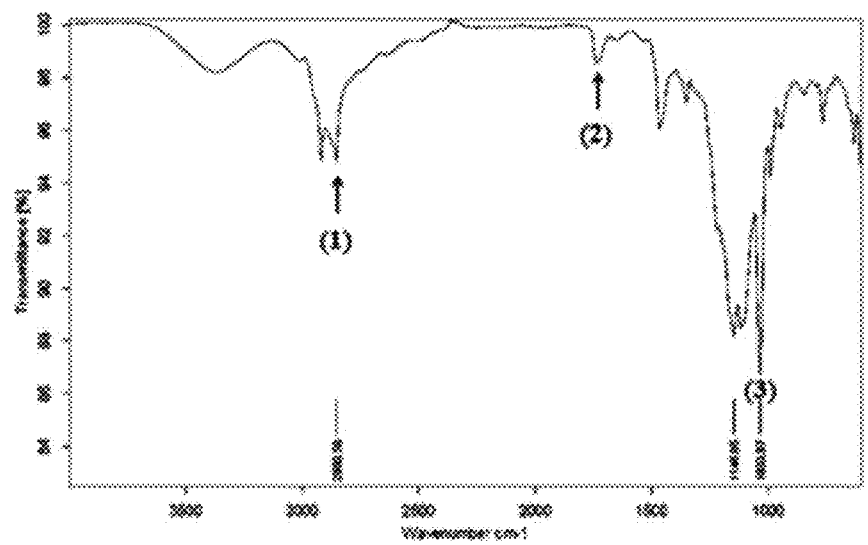
FIG. 9B illustrates ATR-FTIR of the mPEG-DSPE.

FIG. 9A illustrates the ATR-FTIR of co-encapsulated nano-liposomes. FIG. 9B illustrates the mPEG-DSPE of co-encapsulated nano-liposomes It can be seen that alterations in chemical bonds of co-encapsulated nano-liposomes were negligible. In other words, the surface of co-encapsulated nano-liposomes was PEGylated. Referring to FIG. 9B, the mPEG-DSPE bonds emerged in 2,850 cm-1 (CH× stretch, denoted in this FIG by label (1)), 1,750 cm-1 (C=O stretch, which denoted by (2)), and 1,033 cm-1 (C—O stretch, P=O "phosphate", which denoted in this FIG by (3)).

Figure 10A:
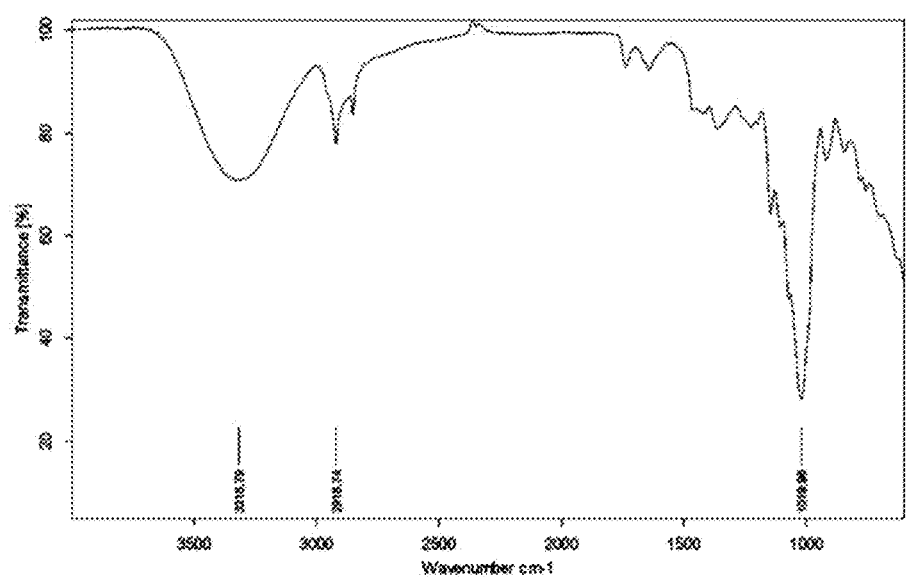
FIG. 10A is ATR-FTIR of the non-targeted-encapsulated nano-liposome according to one or more aspects.
Figure 10B:
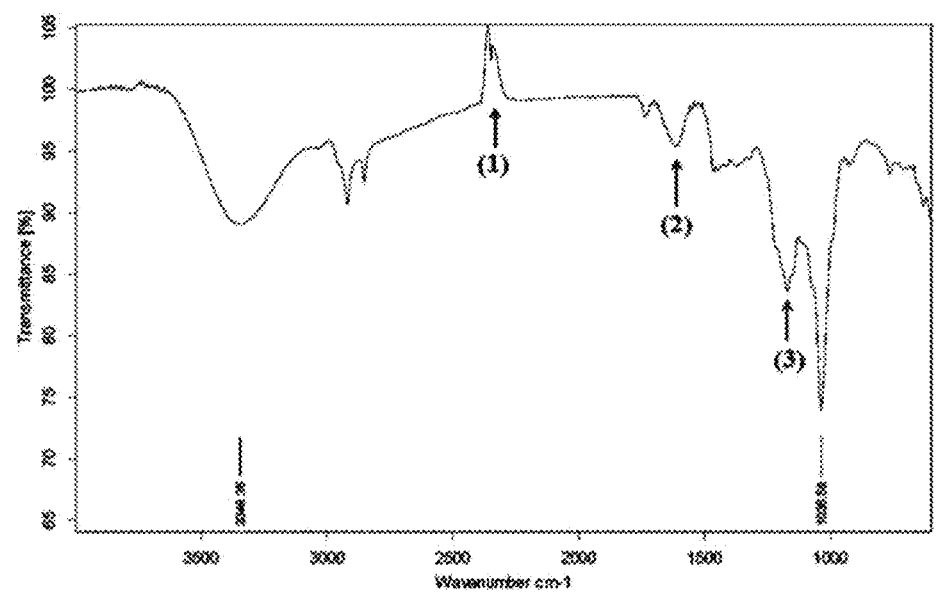
FIG. 10B is ART-FIR of the targeted co-encapsulated nano-liposomes with HAb18 according to one or more aspects.

FIG. 10A illustrates the ATR-FTIR of non-targeted co-encapsulated nano-liposomes and in FIG. 10B, the targeted co-encapsulated nano-liposomes with HAb18 is illustrated. As represented in FIG. 10B, alterations in chemical bonds of targeted co-encapsulated nano-liposomes, represents HAb18 monoclonal antibody bonds. Chemical bonds of HAb18 monoclonal antibody emerged in 2,350 cm-1 (C=_N, which denoted by (1)), 1,655 cm-1 (Amide I, C=N, which denoted in this Fig by (2)), and 1,200 cm-1 (C—N stretch, which denoted in this FIG by (3)). In other words, the surface of co-encapsulated nano-liposomes was targeted with HAb18 monoclonal antibody.

The conjugation of co-encapsulated nano-liposomes with monoclonal antibody was analyzed qualitatively by High-Performance Liquid Chromatography (HPLC) method as illustrated in FIG. 11A to 11D. About 60 μl of the suspensions of co-encapsulated nano-liposomes (0.1 gr/ml), targeted co-encapsulated nano-liposomes (0.1 gr/ml), solution of Hepes buffer and monoclonal antibody HAb18 with same concentrations were analyzed by the HPLC system. A reversed phase of C18 column was used. The mobile phase consisted of sodium phosphate-150 mM pH=7 (100%, v/v) delivered at a flow rate of 1.00 ml/minute. Column elute was monitored spectrophotometrically at the wavelength of 214 nm with a UV detector.

Figure 11A:
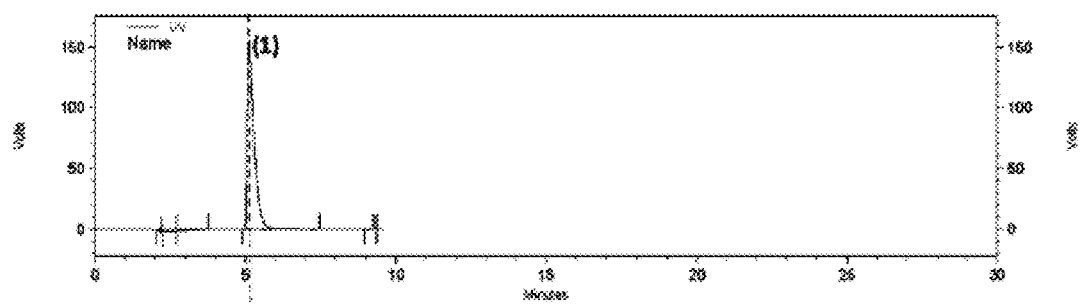
FIG. 11A is the HPLC peaks of Hepes buffer.
Figure 11B:
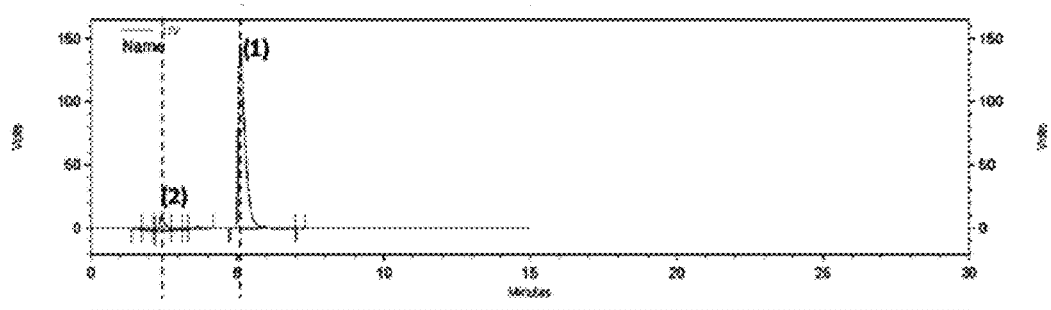
FIG. 11B is the HPLC peaks of non-targeted co-encapsulated nano-liposomes.
Figure 11C:
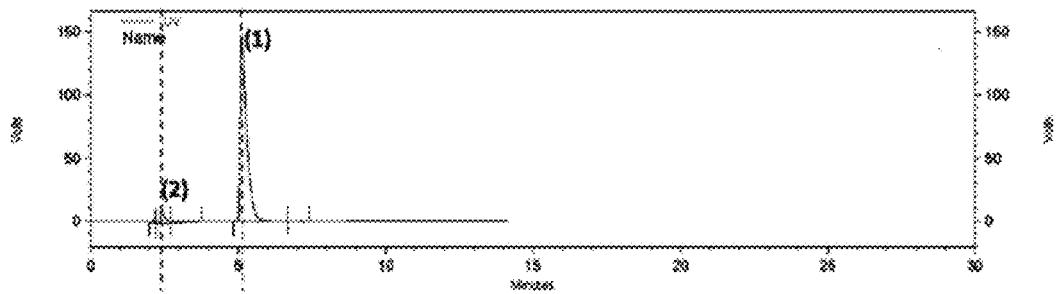
FIG. 11C is the HPLC peaks of HAb18 monoclonal antibody.
Figure 11D:
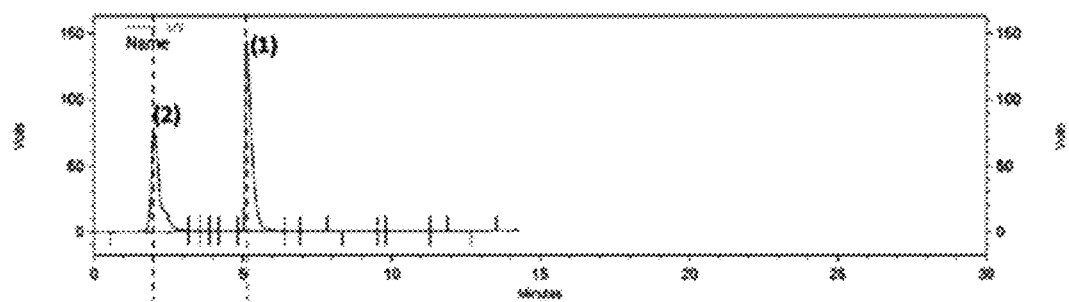
FIG. 11D is the HPLC peaks of targeted co-encapsulated nano-liposomes with HAb18, according to one or more aspects.

Referring to FIG. 11A, this figure illustrates the HPLC peaks of Hepes buffer). The HPLC peak of Hepec buffer in FIGS. 11A to 11D denoted by (1). The HPLC peak which denoted by (2), in FIG. 11B represents the peak of non-targeted co-encapsulated nano-liposomes; in FIG. 11C is the monoclonal antibody HAb18; and in FIG. 11D represents the targeted co-encapsulated nano-liposomes with HAb18. The surface of co-encapsulated nano-liposomes was bioconjugated with monoclonal antibody and FIG. 11, in general, confirms the conjugation of monoclonal antibody with the PEG2000-DSPE on the surface of co-encapsulated nano-liposomes.

Figure 12:
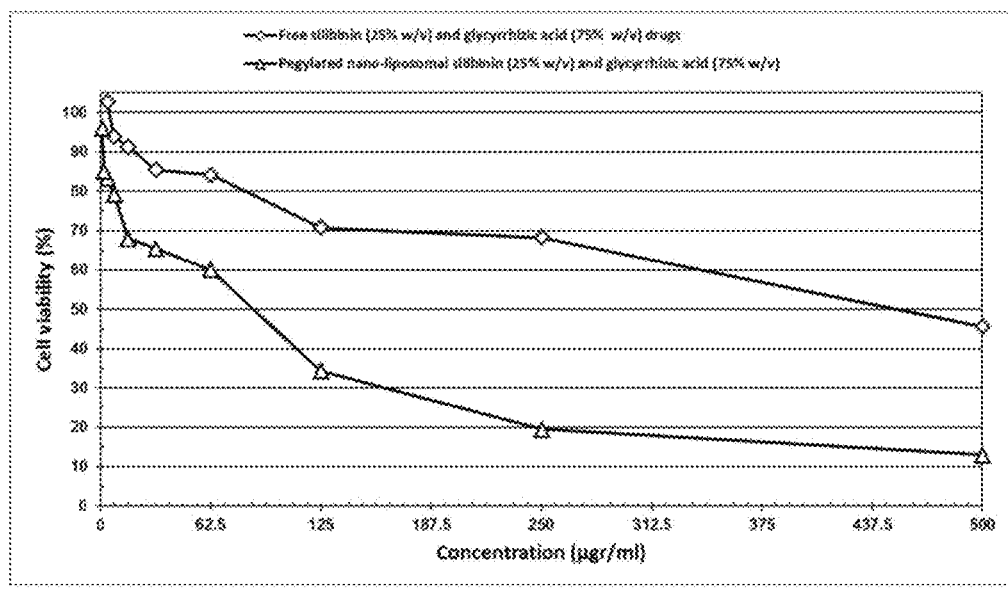
FIG. 12 illustrates cell viability (expressed as mean±standard deviation (SD), and error bars with 5% value) of co-encapsulated nano-liposomes and free silibinin (25% w/v) and glycyrrhizic acid (75% w/v) drugs on HepG2 cell line.

Cytotoxicity of the targeted and non-targeted PEGylated nanoliposomal silibinin (25% w/v) and glycyrrhizic acid (75% w/v), and free silibinin (25% w/v) and glycyrrhizic acid (75% w/v) drugs was examined at different concentrations based on MTT technique and the results illustrated in FIG. 12. While maximum release occurred in the first 48 hours, highest cytotoxicity was examined at this time on HepG2 and fibroblast cell lines. The light absorbance was measured at 540 nm by spectrophotometer.

With further reference to FIG. 12, this figure shows the cell viability of co-encapsulated nano-liposomes, and free silibinin (25% w/v) and glycyrrhizic acid (75% w/v) drugs on HepG2 cell line. FIG. 12 confirms the low cell viability in case of using co-encapsulated nano-liposome on HepG2 cell line.

In vitro study showed that nano-liposome encapsulation of silibinin with glycyrrhizic acid increased the biological activity of free drugs, increased the stability of silibinin and synergized the therapeutic effect of silibinin with glycyrrhizic acid on Hepatocellular carcinoma cell line.

Figure 13:
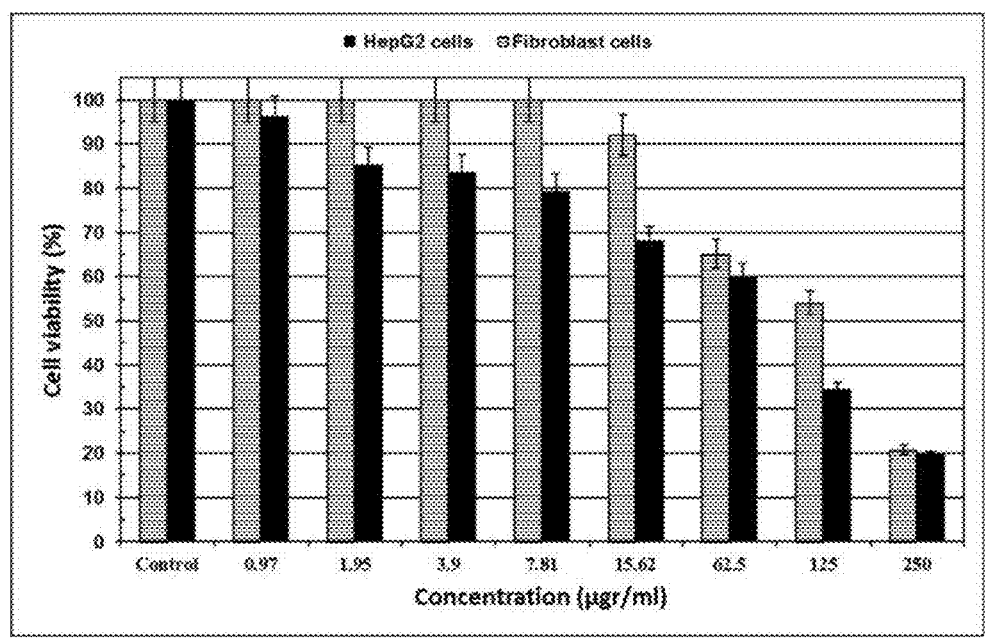
FIG. 13 illustrates the cell viability (expressed as mean±SD, and error bars with 5% value) of co-encapsulated nano-liposomes on HepG2 and fibroblast cell lines.

Referring to FIG. 13, this figure illustrates the cell viability of co-encapsulated nano-liposomes on HepG2 and fibroblast cell lines. The IC50 for pegylated nano liposomal silibinin and glycyrrhizic acid on HepG2 and fibroblast cell line were 48.67, 105.45 μg/ml, the cytotoxicity of pegylated nanoliposomal silibinin and glycyrrhizic acid was about 9 to 11 multiple of free herbal drugs on HepG2 cell line, while, the cytotoxicity of pegylated nanoliposomal silibinin and glycyrrhizic acid on HepG2 cell line was about two times greater than the its cytotoxicity on fibroblast cell line.

In addition, the cytotoxicity of targeted pegylated nanoliposomal silibinin and glycyrrhizic acid was determined which was about 30 to 40 multiple of free herbal drugs on HepG2 cell line, while the cytotoxicity of targeted pegylated nanoliposomal silibinin and glycyrrhizic acid was about 3 to 4 multiple of non-targeted pegylated nanoliposomal silibinin and glycyrrhizic acid on HepG2 cell line.

Figure 14:
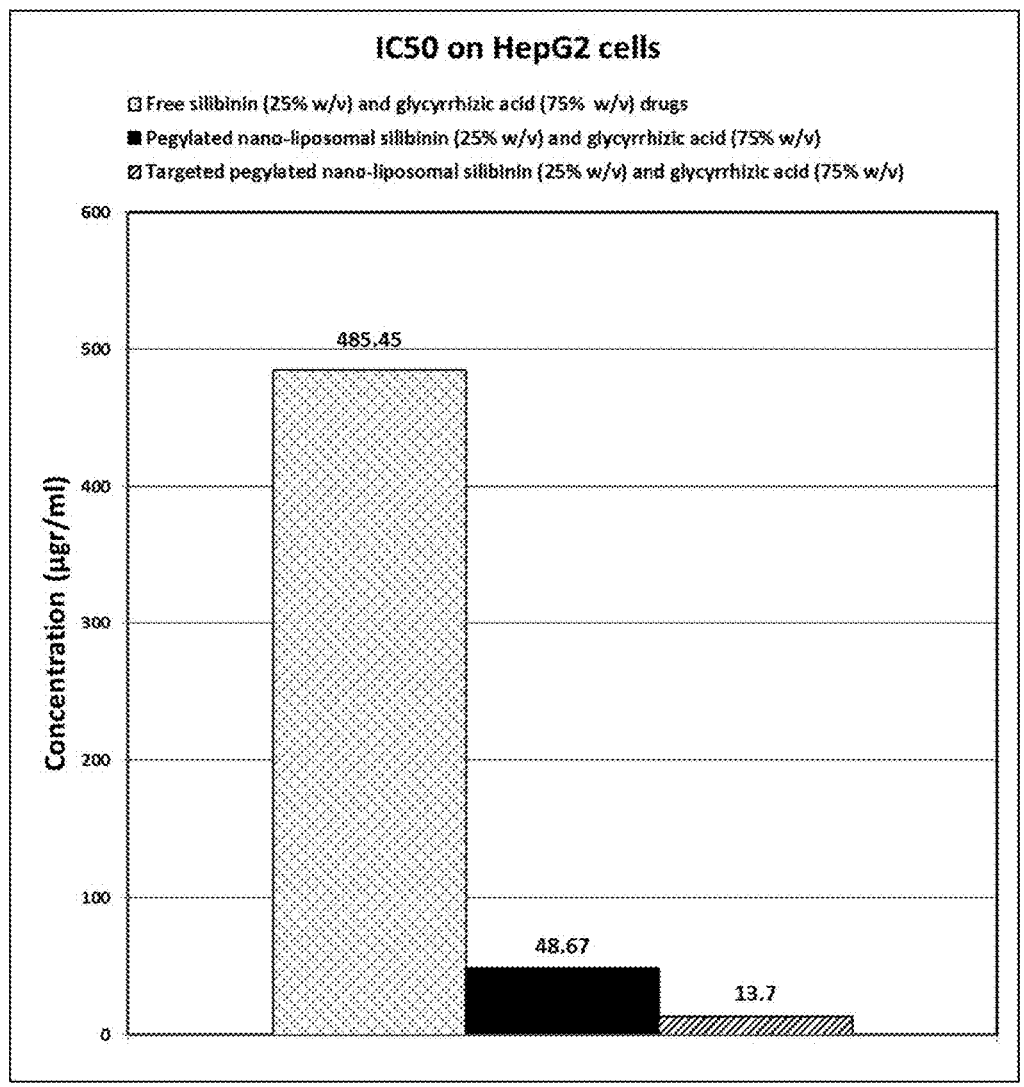
FIG. 14 illustrates the IC50 (expressed as mean±standard SD) of targeted and non-targeted co-encapsulated nano-liposomes and free silibinin (25% w/v) and glycyrrhizic acid (75% w/v) drugs on HepG2 cells.

With reference now to FIG. 14, this figure illustrates the IC50 of targeted and non-targeted co-encapsulated nano-liposomes and free silibinin (25% w/v) and glycyrrhizic acid (75% w/v) drugs on HepG2 cells. The IC50 for targeted and non-targeted the two herbal drugs co-encapsulated nanoliposome compositions, and free silibinin and glycyrrhizic acid drugs on HepG2 cell line were 13.7, 48.67, 485.45 μg/ml. As indicated by this figure, the cytotoxicity of targeted PEGylated nanoliposomal silibinin and glycyrrhizic acid was about 35 times greater than the cytotoxicity of free herbal drugs on HepG2 cell line and the cytotoxicity of targeted PEGylated nanoliposomal silibinin and glycyrrhizic acid was about 3.5 times greater than the cytotoxicity of non-targeted PEGylated nanoliposomal silibinin and glycyrrhizic acid on HepG2 cell line. Values are expressed as mean.

What is claimed is:

1. A liposome composition for the treatment of cancer, comprising: at least a phospholipid compound; cholesterol; and at least two herbal drugs, wherein:
said at least two herbal drugs are co-encapsulated in the liposome composition, and
one of the at least two herbal drugs is silibinin and another of the at least two herbal drugs is glycyrrhizic acid,
the mass ratio of silibinin to glycyrrhizic acid is approximately 1:3, and the liposome comprises poly(ethylene glycol)-phospholipid conjugate (PEG-lipid).

2. The liposome composition of claim 1, wherein the at least one phospholipid compound comprises dipalmitoyl phosphatidyl choline (DPPC).

3. The liposome composition of claim 2, wherein the PEG-lipid is distearoyl-phosphatidylethanolamine-N-[methoxy(polyethene glycol)-2000 (DSPE-mPEG2000).

4. The liposome composition of claim 3, wherein the molar ratio of (DPPC):cholesterol:DSPE-mPEG2000 in the liposome is in the rang of about 7:3:5:0.3 to about 7:4:0.4.

5. The liposome composition of claim 1, wherein the weight ratio of silibinin:glycyrrhizic acid:lipid phase is in the range of about 1:3:7 to 1:3:11.

6. The liposome composition of claim 1, wherein the liposome composition has a negative zeta potential.

7. The liposome composition of claim 1, wherein said liposome composition has an average diameter of less than 50 nanometers.

8. A targeted liposome composition for the treatment of cancer comprising:
at least one phospholipid compound;
a poly(ethylene glycol)-phospholipid conjugate (PEG-lipid);
cholesterol;
at least one monoclonal antibody; and
at least two herbal drugs co-encapsulated in the liposome composition, wherein:
one of the at least two herbal drugs is silibinin,
another one of the at least two herbal drugs is glycyrrhizic acid, and
glycyrrhizic acid is present at approximately three times the mass of silibinin.

9. The targeted liposome composition of claim 8, wherein the at least two herbal drugs co-encapsulated in the liposome composition include a third member selected from the group consisting of isosilibinin, silichristin, silidanin, glycyrrhetinic acid and combinations thereof.

10. The targeted liposome composition of claim 8, wherein the targeted liposome composition has an average diameter of less than about 90 nanometers.

11. The targeted liposome composition of claim 8, wherein the monoclonal antibody is selected from the group consisting of anti-CD147, HAb18, anti-CD166, anti-CD20, anti-HER2, anti-VEGF-A, anti-EGFR and rituximab.

12. The targeted liposome composition of claim 8, wherein said monoclonal antibody is Hab18 monoclonal antibody.

13. The targeted liposome composition of claim 12, wherein the number of Hab18 monoclonal antibodies on the surface of the liposome is at least 6.

14. The targeted liposome composition of claim 8, wherein the at least one phospholipid comprises dipalmitoyl phosphatidyl choline (DPPC).

15. The targeted liposome composition of claim 8, wherein the PEG-lipid is distearoyl-phosphatidylethanolamine-N-[methoxy(polyethene glycol)-2000 (DSPE-mPEG2000).

16. The targeted liposome composition of claim 8, wherein the phospholipid component comprises dipalmitoyl phosphatidyl choline (DPPC), wherein the PEG-lipid is distearoyl-phosphatidylethanolamine-N-[methoxy(polyethylene glycol)-2000] (DSPE-PEG), and wherein the molar ratio of (DPPC):cholesterol:DSPE-mPEG2000 in the liposome composition is in the range of about 7:3.5:0.3 to about 7:4:0.4.

17. The targeted liposome composition of claim 16, wherein the targeted liposome composition has a negative zeta potential.

18. A method of preparing the liposome composition of claim 1, the method comprising:
mixing a lipid mixture with the at least two herbal drugs in a solvent;

evaporating the solvent from a result of mixing the lipid mixture with the at least two herbal drugs to form a lipid film;

hydrating the lipid film with an aqueous solvent to form multilamellar vesicles; and sonicating the multilamellar vesicles to form a co-encapsulated nano-liposome composition that simultaneously includes the at least two herbal drugs co-encapsulated.

19. The method of claim 18, wherein hydrating the lipid film with the aqueous solvent is performed in a buffer.

20. The method of claim 19, wherein the at least one phospholipid compound comprises dipalmitoyl phosphatidyl choline (DPPC).

21. The method of claim 20, wherein the PEG-lipid is distearoyl-phosphatidylethanolamine-N-[methoxy (polyethene glycol)-2000] (DSPE-mPEG2000).

22. The method of claim 21, wherein the specific molar ratio of DPPC:cholesterol:DSPE-mPEG2000 is in the range of about 7:3.5:0.3 to about 7:4:0.4.

23. The method of claim 18, wherein hydrating the lipid film with the aqueous solvent is performed in a buffer, and wherein the specific weight ratio of the at least two herbal drugs:the lipid mixture:the aqueous solvent in the buffer is in the range of about 1:2:7 to about 1:3:11.

24. The method of claim 18, further comprising: drying of the liposome composition.

25. A method for preparing the liposome composition of claim 10, the method comprising:

mixing a lipid mixture with the at least two herbal drugs in a solvent;

evaporating the solvent from a result of mixing the lipid mixture with the at least two herbal drugs to form a lipid film;

hydrating the lipid film with an aqueous solvent to form multilamellar vesicles;

sonicating the multilameral vesicles to form a co-encapsulated nano-liposome composition that simultaneously includes the at least two herbal drugs co-encapsulated; and adding the monoclonal antibody to the prepared liposome composition to form the targeted liposome composition.

26. The method of claim 25, wherein the monoclonal antibody is selected from the group consisting of anti: HER2, anti-VEGF-A, and anti-EGFR.

27. The method of claim 25, wherein the monoclonal antibody is Hab18 monoclonal antibody.

28. The method of claim 25, wherein the method provides a loading efficacy in a range of about 25% to about 70% for the at least two herbal drugs.

29. The method of claim 25, wherein the liposome composition has an average diameter of less than about 90 nanometers.

30. The method of claim 18, wherein the method provides a loading efficacy in a range of about 25% to about 70% for the at least two herbal drugs.

31. The method of claim 18, wherein the liposome composition has an average diameter of less than about 90 nanometers.

32. A method of treating cancer in an individual in need of liver cancer treatment comprising administering the liposome composition of claim 1 to said individual.

33. A method of treating liver cancer in an individual in need of liver cancer treatment comprising administering the liposome composition of claim 8 to said individual.

* * * * *